United States Patent
Bain

(10) Patent No.: US 11,468,480 B2
(45) Date of Patent: *Oct. 11, 2022

(54) SYSTEM AND METHOD FOR HEALTH RISK EVALUATION

(71) Applicant: Salucro Healthcare Solutions, LLC, Phoenix, AZ (US)

(72) Inventor: S. Clayton Bain, Phoenix, AZ (US)

(73) Assignee: SALUCRO HEALTHCARE SOLUTIONS, LLC, Phoenix, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/321,867

(22) Filed: May 17, 2021

(65) Prior Publication Data

US 2021/0279770 A1 Sep. 9, 2021

Related U.S. Application Data

(63) Continuation of application No. 15/363,635, filed on Nov. 29, 2016, now Pat. No. 11,042,908.

(Continued)

(51) Int. Cl.
*G06Q 30/02* (2012.01)
*G16H 50/30* (2018.01)
(Continued)

(52) U.S. Cl.
CPC ......... *G06Q 30/0269* (2013.01); *G06Q 10/10* (2013.01); *G06Q 30/0276* (2013.01);
(Continued)

(58) Field of Classification Search
CPC .............. G06Q 30/0269; G06Q 10/10; G06Q 30/0276; G06Q 30/0277; G16H 40/67; G16H 50/30
(Continued)

(56) References Cited

U.S. PATENT DOCUMENTS

| 2004/0213020 A1 | 10/2004 | Gotfried |
| 2011/0082727 A1 | 4/2011 | Macias |

(Continued)

FOREIGN PATENT DOCUMENTS

| AU | 2005289834 A1 * | 4/2007 | ......... G06F 19/3456 |
| KR | 20130126395 | 11/2013 | |

OTHER PUBLICATIONS

Eva K Laan, Effectiveness of a web-based health risk assessment with individually-tailored feedback on lifestyle behaviour: study protocol, 2012 (Year: 2012).*

(Continued)

*Primary Examiner* — Tarek Elchanti
(74) *Attorney, Agent, or Firm* — Snell & Wilmer L.L.P.

(57) ABSTRACT

A system for evaluating health risk is provided. The system may be configured for requesting first data from a merchant associated with a user and second data from an activity tracking service associated with the user. The system may also comprise analyzing the item to determine a first health impact for the item based on the item and demographic information associated with the user. The system may further comprise analyzing the level of activity to determine a second health impact from the level of activity based on the level of activity and the demographic information associated with the user. The system may further comprise selecting an advertisement based on medical data, and at least one of the first health impact, the second health impact and the demographic information associated with the user.

19 Claims, 6 Drawing Sheets

Related U.S. Application Data

(60) Provisional application No. 62/262,796, filed on Dec. 3, 2015.

(51) Int. Cl.
*G16H 40/67* (2018.01)
*G06Q 10/10* (2012.01)

(52) U.S. Cl.
CPC ......... *G06Q 30/0277* (2013.01); *G16H 40/67* (2018.01); *G16H 50/30* (2018.01)

(58) Field of Classification Search
USPC ....................................... 705/14.67; 600/301
See application file for complete search history.

(56) References Cited

U.S. PATENT DOCUMENTS

| | | |
|---|---|---|
| 2011/0166889 A1 | 7/2011 | Bain |
| 2013/0073303 A1 | 3/2013 | Hsu |
| 2013/0228623 A1 | 9/2013 | Virella |
| 2013/0339052 A1 | 12/2013 | Neff |

OTHER PUBLICATIONS

Andreas E. Stuck, et al., "Effect of Health Risk Assessment and Counselling on Health Behaviour and Survival in Older People: A Pragmatic Randomised Trial", 2015 (Year: 2015).

Laila Nadime, "Analytical Methods to Support Risk Identification and Analysis in Healthcare Systems", 2011 (Year 2011).

Eva K. Laan, et al., "Effectiveness of a web-based health risk assessment with individually-tailored feedback on lifestyle behaviour: study protocol", 2012 (Year: 2012).

USPTO, Non-Final Office Action dated May 7, 2020 in U.S. Appl. No. 15/363,635.

USPTO, Final Office Action dated Aug. 27, 2020 in U.S. Appl. No. 15/363,635.

USPTO, Advisory Action dated Oct. 5, 2020 in U.S. Appl. No. 15/363,635.

USPTO, Non-Final Office Action dated Jan. 19, 2021 in U.S. Appl. No. 15/363,635.

USPTO, Final Office Action dated Feb. 10, 2021 in U.S. Appl. No. 15/363,635.

USPTO, Notice of Allowance dated Mar. 29, 2021 in U.S. Appl. No. 15/363,635.

\* cited by examiner

```
                                                          600
┌─────────────────────────────────────────────────────────────┐
│ REQUESTING FIRST DATA FROM A MERCHANT ASSOCIATED WITH A     │
│ USER AND SECOND DATA FROM AN ACTIVITY TRACKING SERVICE      │
│ ASSOCIATED WITH THE USER                             610    │
└─────────────────────────────────────────────────────────────┘
                              │
┌─────────────────────────────────────────────────────────────┐
│ PARSING THE FIRST DATA TO DETERMINE AN ITEM PURCHASED FROM  │
│ THE MERCHANT                                         620    │
└─────────────────────────────────────────────────────────────┘
                              │
┌─────────────────────────────────────────────────────────────┐
│ ANALYZING THE ITEM TO DETERMINE A FIRST HEALTH IMPACT FOR THE│
│ ITEM BASED ON THE ITEM AND DEMOGRAPHIC INFORMATION          │
│ ASSOCIATED WITH THE USER                             630    │
└─────────────────────────────────────────────────────────────┘
                              │
┌─────────────────────────────────────────────────────────────┐
│ PARSING THE SECOND DATA TO DETERMINE A LEVEL OF ACTIVITY    │
│ MONITORED BY THE ACTIVITY TRACKING SERVICE                  │
│                                                      640    │
└─────────────────────────────────────────────────────────────┘
                              │
┌─────────────────────────────────────────────────────────────┐
│ ANALYZING THE LEVEL OF ACTIVITY TO DETERMINE A SECOND HEALTH│
│ IMPACT FROM THE LEVEL OF ACTIVITY BASED ON THE LEVEL OF     │
│ ACTIVITY AND THE DEMOGRAPHIC INFORMATION ASSOCIATED WITH    │
│ THE USER                                             650    │
└─────────────────────────────────────────────────────────────┘
                              │
┌─────────────────────────────────────────────────────────────┐
│ EVALUATING A HEALTH RISK OF THE USER BASED ON THE FIRST     │
│ HEALTH IMPACT, THE SECOND HEALTH IMPACT AND THE DEMOGRAPHIC │
│ INFORMATION ASSOCIATED WITH THE USER                 660    │
└─────────────────────────────────────────────────────────────┘
                              │
┌─────────────────────────────────────────────────────────────┐
│ SELECTING AN ADVERTISEMENT BASED ON MEDICAL DATA, AND AT    │
│ LEAST ONE OF THE FIRST HEALTH IMPACT, THE SECOND HEALTH     │
│ IMPACT OR THE DEMOGRAPHIC INFORMATION ASSOCIATED WITH THE   │
│ USER                                                 670    │
└─────────────────────────────────────────────────────────────┘
```

FIGURE 6

SYSTEM AND METHOD FOR HEALTH RISK EVALUATION

CROSS REFERENCE TO RELATED APPLICATIONS

This application is a continuation of, claims priority to and the benefit of, U.S. Ser. No. 15/363,635 filed on Nov. 29, 2016 and entitled "System And Method For Health Risk Evaluation." The '635 application claims priority to, and the benefit of, U.S. Provisional Patent Application Ser. No. 62/262,796, entitled "System and Method For Health Risk Evaluation" filed Dec. 3, 2015. All of which are hereby incorporated by reference in their entireties for all purposes.

FIELD

The present disclosure generally relates to providing incentives to patients, and more particularly, to providing incentives to patients for demonstrating desirable behaviors and determining risks associated with the items consumed by the patients and the activity level of the patients.

BACKGROUND

The ability to gauge the health risk of a patient based on parameters associated with a patient's everyday life and habits provides a healthcare provider with a more holistic understanding of the patient's needs. As such, it would be desirable to understand the activity level of the patient and the items that the patient consumes to understand the health risks associated with a patient.

Moreover, user payment systems allow a user to access an account, via a web client, telephone system, or similar portal to view accounts, initiate payments, view actions associated with accounts, view documents associated with accounts and the like. Further, these systems acquire and include user specific information, which allows the system to characterize the preferences of a user automatically. Many of these systems are employed by healthcare providers, for example, hospitals, clinics, medical practice groups, and the like. With the rising cost of healthcare, there is a need to reduce the total cost of health services provided. Further, there is a need to provide cost effective, discounted and targeted items to a user.

SUMMARY

In various embodiments, a system, method, and computer readable medium (collectively, the "System") for evaluating health risks are provided. The System may be configured to perform operations and/or steps comprising requesting, by the computer based system, first data from a merchant associated with a user and second data from an activity tracking service associated with the user. The system may further comprise parsing, by the computer based system, the first data to determine an item purchased from the merchant. The system may also comprise analyzing, by the computer based system, the item to determine a first health impact for the item based on the item and demographic information associated with the user. The system may further comprise parsing, by the computer based system, the second data to determine a level of activity monitored by the activity tracking service. The system may further comprise analyzing, by the computer based system, the level of activity to determine a second health impact from the level of activity based on the level of activity and the demographic information associated with the user. The system may further comprise selecting, by the computer based system, an advertisement based on medical data, and at least one of the first health impact, the second health impact and the demographic information associated with the user.

In various embodiments, the system may further comprise receiving, by the computer based, a selection of a bill associated with the user, and allocating, by the computer based system, an incentive based on the advertisement. The system may further comprise crediting, by the computer based system, the incentive to an account, wherein the account is at least one of owned by the user or associated with the user. The account may be configured to accumulate incentives that may be applied to bills. The system may further comprise crediting, by the computer based system, the incentive to a bill associated with the user.

In various embodiments, the system may further comprise reducing, by the computer based system, an amount of the bill, and receiving, by the computer based system, a payment for the bill. The advertisement may include at least one of a product and a service associated with medical data associated with the patient.

In various embodiments, the system may further comprise displaying, by the computer based system, the advertisement for a predetermined amount of time. The system may further comprise by the computer based system, a selection of the advertisement and presenting, by the computer based system, an offer based on the advertisement for an offered item, wherein the offered item is associated with the medical data.

In various embodiments, the activity tracking system may include a wearable device that is connected to a portable electronic device and is configured to interface with a user information engine. The activity tracking system may also include a network tracking system that is connected to a portable electronic device and is configured to interface with a user information engine.

In various embodiments, the system may further comprise evaluating, by the computer based system, a health risk of the user based on the first health impact, the second health impact and the demographic information associated with the user.

BRIEF DESCRIPTION OF THE DRAWINGS

A more complete understanding of the present disclosure may be derived by referring to the detailed description and claims when considered in connection with the Figures, wherein like reference numbers refer to similar elements throughout the Figures, and:

FIG. 6 is a process flow illustrating an exemplary customer evaluation method, in accordance with various embodiments.

DETAILED DESCRIPTION

Figure 1:
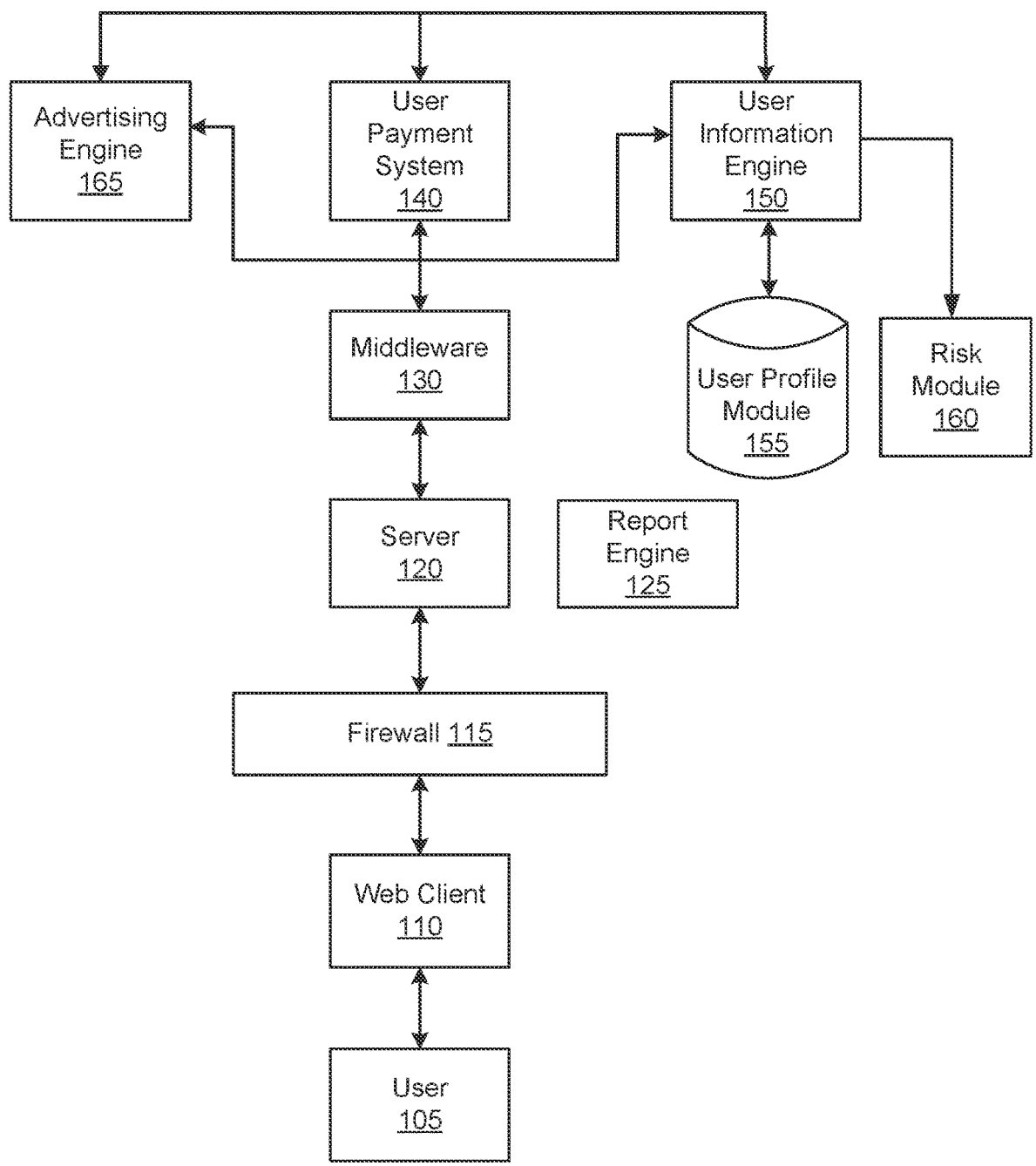
FIG. 1 is a block diagram illustrating major system components for providing advertisements to a user of a user payment system, in accordance with various embodiments.

The detailed description herein is presented for purposes of illustration only and not of limitation. For example, the steps recited in any of the method or process descriptions may be executed in any order and are not limited to the order presented. For the sake of brevity, conventional data networking, application development and other functional aspects of the systems (and components of the individual operating components of the systems) may not be described in detail herein.

The systems and methods include a unique combination of one or more features associated with a user payment system. In various embodiments, the user payment system may be configured with an advertising engine, such that the advertising engine may provide targeting advertisements to a user. Advertising revenue is accrued from the advertisements. The revenue may be allocated to various sources including the user, the user payment system provider, a hospital, a healthcare provider, and/or the like. For more information regarding advertising revenue distribution systems, see U.S. Ser. No. 14/052,529 entitled "SYSTEM AND METHOD FOR ADVERTISING REVENUE DISTRIBUTION", filed on Oct. 10, 2013; U.S. Ser. No. 12/985,217 entitled "SYSTEM AND METHOD FOR ADVERTISING REVENUE DISTRIBUTION", filed on Jan. 5, 2011; and U.S. Provisional Patent Application No. 61/292,332, filed Jan. 5, 2010, entitled "System and Method for Advertising Revenue Distribution," all of which are incorporated by reference in their entireties for all purposes.

"User" may include any individual, consumer, patient, group, business, organization, government entity, benefits administrator, user payment system provider, account holder, charitable organization, software, hardware, and/or any other entity.

An "account", "account number" or "consumer account" as used herein, may include any device, code (e.g., one or more of an authorization/access code, personal identification number ("PIN"), Internet code, other identification code, and/or the like), number, letter, symbol, digital certificate, smart chip, digital signal, analog signal, biometric or other identifier/indicia suitably configured to allow the consumer to access, interact with or communicate with the system. The account number may optionally be located on or associated with a rewards account, charge account, credit account, debit account, prepaid account, telephone card, embossed card, smart card, magnetic stripe card, bar code card, transponder, radio frequency card or an associated account. The system may include or interface with any of the foregoing accounts or devices, or a transponder and RFID reader in RF communication with the transponder (which may include a fob). Typical devices may include, for example, a key ring, tag, card, cell phone, wristwatch or any such form capable of being presented for interrogation. Moreover, the system, computing unit or device discussed herein may include a "pervasive computing device," which may include a traditionally non-computerized device that is embedded with a computing unit.

A "user payment system" or "user payment account" may include any account that may be used to facilitate a financial transaction.

A "user payment system provider" or "user payment account provider" includes any entity that offers user payment account services to consumers. Although often referred to as a "financial institution," the financial institution may represent any type of bank, lender or other type of account issuing institution, such as payment services organizations. It is further noted that other participants may be involved in some phases of the transaction, such as an intermediary settlement institution.

A "financial processor," "payment network," or "payment system" or may include any software, hardware and/or entity which processes transactions, issues accounts, acquires financial information, settles accounts, conducts dispute resolution regarding accounts, and/or the like. As one of ordinary skill will recognize a financial account issuer may operate as, and provide the functions and services of a financial processor.

Phrases and terms similar to an "item" may include any good, service, information, experience, entertainment, data, offer, discount, rebate, points, virtual currency, content, access, rental, lease, contribution, account, credit, debit, benefit, right, reward, points, coupons, credits, monetary equivalent, anything of value, something of minimal or no value, monetary value, non-monetary value and/or the like. Moreover, the "transactions" or "purchases" discussed herein may be associated with an item. Furthermore, a "reward" may be an item.

With reference to FIG. 1, system 100 facilitates interaction between a user 105 and a user payment account system ("UPAS") 140 through, in various embodiments, a web client 110 with a network connection to an Internet server 120 by way of the Internet. In various embodiments, Internet server 120 employs an authentication server to validate credentials, assign proper permissions, and retrieve preferences information for authorized consumers of UPAS 140. In various embodiments, Internet server 120 employs an application server to manage various applications and utilities that are utilized by system 100. In various embodiments, Internet server 120 interacts directly with the various systems and components disclosed herein. System 100 may include any number of computing platforms and databases that may be commonly found within a typical user payment system environment (e.g., at a payment processor, account issuer system, payment network, transactions database, etc.).

Such systems may include, for example, a user information engine 150, a user profile module 155, a risk module 160, an advertising engine 165, and the like. Other systems may include, for example, new accounts systems, management information systems, business information systems, third-party data providers and the like. Each of the systems may be interconnected within by a network in via any method and/or device described herein.

A middleware server and/or application 130 may serve as an intermediary between the various systems to ensure appropriate communications between disparate platforms. A report engine 125 retrieves and/or is provided with data from the various systems in order to generate billing statements, reports, and the like.

UPAS 140 or any other components discussed herein may further include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases.

As will be appreciated by one of ordinary skill in the art, one or more of the components of system 100 may be embodied as a customization of an existing system, an add-on product, upgraded software, a stand alone system (e.g., kiosk), a distributed system, a method, a data processing system, a device for data processing, a computer and/or a computer program product. Accordingly, individual system 100 components may take the form of an entirely software embodiment, an entirely hardware embodiment, or an embodiment combining aspects of both software and hardware. In various embodiments, a system 100 component (e.g. a computer) may include a processor, a memory, a communications interface, a network interface, etc. Furthermore, individual system 100 components may take the form of a computer program product on a computer-readable storage medium having computer-readable program code means embodied in the storage medium. Any suitable computer-readable storage medium may be utilized, including hard disks, CD-ROM, flash memory, optical storage devices, magnetic storage devices, and/or the like. In various embodiments, a system 100 component and/or subsystem comprises a network interface communicating with a memory, the memory communicating with a processor; and the processor, when executing a computer program, configured to accomplish a variety of functions and/or steps.

The system contemplates uses in association with web services, utility computing, pervasive and individualized computing, security and identity solutions, autonomic computing, commodity computing, mobility and wireless solutions, open source, biometrics, grid computing and/or mesh computing.

User 105 may include any entity that utilizes system 100. User 105 may also include any entity that has a user payment account with a user payment account provider. User 105 may include a consumer who uses an account code without any physical card, uses a transponder, and/or uses a physical transaction card, to purchase items which are billed on the billing statement discussed herein. User 105 may also select payment terms relating to a revolving line of credit account, submit payments, and/or view billing statements. User 105 may be, for example, a customer who initiates payments. In various embodiments, user 105 may be, for example, a customer who receives incentives for participating in an advertising program during payments. In various embodiments, user 105 may be a consumer service representative or the like who interacts with system 100 to provide account information and configure payment terms or terms on behalf of a user. In various embodiments, user 105 may interface with UPAS 140 via any communication protocol, device or method discussed herein or known in the art. For example, user 105 may interact with UPAS 140 by way of an Internet browser at web client 110.

Web client 110 comprises any hardware and/or software suitably configured to facilitate requesting, retrieving, updating, analyzing, entering and/or modifying data. Web client 110 includes any device (e.g., personal computer) which communicates (in any manner discussed herein) with UPAS 140 via any network discussed herein. Such browser applications comprise Internet browsing software installed within a computing unit or system to conduct online transactions and/or communications. These computing units or systems may take the form of a computer or set of computers, although other types of computing units or systems may be used, including laptops, notebooks, hand held computers, set-top boxes, workstations, computer-servers, main frame computers, mini-computers, PC servers, pervasive computers, network sets of computers, and/or the like. Practitioners will appreciate that web client 110 may or may not be in direct contact with UPAS 140. For example, web client 110 may access the services of UPAS 140 through another server, which may have a direct or indirect connection to Internet server 120.

As those skilled in the art will appreciate, web client 110 includes an operating system (e.g., Windows NT, 95/98/2000/XP/VISTA/7, OS2, UNIX, Linux, Solaris, MacOS, etc.) as well as various conventional support software and drivers typically associated with computers. Web client 110 may include any suitable personal computer, network computer, workstation, minicomputer, mainframe or the like. Web client 110 can be in a home or business environment with access to a network. In various embodiments, access is through a network or the Internet through a commercially available web-browser software package.

Web client 110 may be independently, separately or collectively suitably coupled to the network via data links which includes, for example, a connection to an Internet Service Provider (ISP) over the local loop as is typically used in connection with standard modem communication, cable modem, Dish networks, ISDN, Digital Subscriber Line (DSL), or various wireless communication methods, see, e.g., Gilbert Held, Understanding Data Communications (1996), which is hereby incorporated by reference. It is noted that the network may be implemented as other types of networks, such as an interactive television (ITV) network.

Web client 110 may include any number of applications, code modules, cookies, and the like to facilitate interaction with UPAS 140 in order to, for example, make a payment, view an advertising program, view statements, view payment terms, view spend information, elect a payment term, submit/authorize a payment, and the like. In various embodiments, web client 110 may store user 105 preferences and/or any other information disclosed herein on a hard drive or any other local memory device. Accordingly, web client 110 may retrieve and store user information within a memory structure of web client 110 in the form of a browser cookie, for example. In another embodiment, web client 110 retrieves information relating to user 105 from UPAS 140 on establishing a session with Internet server 120.

Firewall 115, as used herein, may comprise any hardware and/or software suitably configured to protect UPAS 140 components from users of other networks. Firewall 115 may reside in varying configurations including stateful inspection, proxy based and packet filtering among others. Firewall 115 may be integrated as software within Internet server 120, any other UPAS 140 components or may reside within another computing device or may take the form of a stand-alone hardware component.

Internet server 120 may include any hardware and/or software suitably configured to facilitate communications between web client 110 and one or more UPAS 140 components. Further, Internet server 120 may be configured to transmit data to web client 110 within markup language documents. As used herein, "data" may include encompassing information such as commands, queries, files, data for storage, and/or the like in digital or any other form. Internet server 120 may operate as a single entity in a single geographic location or as separate computing components located together or in separate geographic locations.

Internet server 120 may provide a suitable web site or other Internet-based graphical user interface which is accessible by consumers. In various embodiments, the Microsoft Internet Information Server (IIS), Microsoft Transaction Server (MTS), and Microsoft SQL Server, are used in conjunction with the Microsoft operating system, Microsoft NT web server software, a Microsoft SQL Server database system, and a Microsoft Commerce Server. Additionally, components such as Access or Microsoft SQL Server, Oracle, Sybase, Informix MySQL, InterBase, etc., may be used to provide an Active Data Object (ADO) compliant database management system.

Any of the communications, inputs, storage, databases or displays discussed herein may be facilitated through a web site having web pages. The term "web page" as it is used herein is not meant to limit the type of documents and applications that might be used to interact with the user. For example, a typical web site might include, in addition to standard HTML documents, various forms, Java applets, JavaScript, active server pages (ASP), common gateway interface scripts (CGI), extensible markup language (XML), dynamic HTML, cascading style sheets (CSS), helper applications, plug-ins, and/or the like. A server may include a web service that receives a request from a web server, the request including a URL (e.g. http://yahoo.com/stockquotes/ge) and an IP address (e.g. 123.4.56.789). The web server retrieves the appropriate web pages and sends the data or applications for the web pages to the IP address. Web services are applications that are capable of interacting with other applications over a communications means, such as the Internet. Web services are typically based on standards or protocols such as XML, SOAP, WSDL and UDDI. Web services methods are well known in the art, and are covered in many standard texts. See, e.g., Alex Nghiem, IT Web Services: A Roadmap for the Enterprise (2003), hereby incorporated by reference.

Middleware 130 may include any hardware and/or software suitably configured to facilitate communications and/or process transactions between disparate computing systems. Middleware components are commercially available and known in the art. Middleware 130 may be implemented through commercially available hardware and/or software, through custom hardware and/or software components, or through a combination thereof. Middleware 130 may reside in a variety of configurations and may exist as a standalone system or may be a software component residing on the Internet server 120. Middleware 130 may be configured to process transactions between the various components of UPAS 140 and any number of internal or external issuer systems 100 for the purposes disclosed herein.

In order to control access to any component of UPAS 140, Internet server 120 may invoke an authentication server (not shown) in response to user 105 submissions of authentication credentials received at Internet server 120 from web client 110. The authentication server may include any hardware and/or software suitably configured to receive authentication credentials, encrypt and decrypt credentials, authenticate credentials, and grant access rights according to privileges (e.g., pre-defined privileges) attached to the credentials. The authentication server may grant varying degrees of application and data level access to users based on information stored within a database and/or any other known memory structure.

One skilled in the art will appreciate that system 100 may employ any number of databases in any number of configurations. Further, any databases discussed herein may be any type of database, such as relational, hierarchical, graphical, object-oriented, and/or other database configurations. Common database products that may be used to implement the databases include DB2 by IBM (White Plains, N.Y.), various database products available from Oracle Corporation (Redwood Shores, Calif.), Microsoft Access or Microsoft SQL Server by Microsoft Corporation (Redmond, Wash.), or any other suitable database product. Moreover, the databases may be organized in any suitable manner, for example, as data tables or lookup tables. Each record may be a single file, a series of files, a linked series of data fields or any other data structure.

Association of certain data may be accomplished through any desired data association technique such as those known or practiced in the art. For example, the association may be accomplished either manually or automatically. Automatic association techniques may include, for example, a database search, a database merge, GREP, AGREP, SQL, using a key field in the tables to speed searches, sequential searches through all the tables and files, sorting records in the file according to a known order to simplify lookup, and/or the like. The association step may be accomplished by a database merge function, for example, using a "key field" in pre-selected databases or data sectors. Various database tuning steps are contemplated to optimize database performance. For example, frequently used files such as indexes may be placed on separate file systems to reduce In/Out ("I/O") bottlenecks.

More particularly, a "key field" partitions the database according to the high-level class of objects defined by the key field. For example, certain types of data may be designated as a key field in a plurality of related data tables and the data tables may then be linked on the basis of the type of data in the key field. The data corresponding to the key field in each of the linked data tables is preferably the same or of the same type. However, data tables having similar, though not identical, data in the key fields may also be linked by using AGREP, for example. In accordance with one aspect of system 100, any suitable data storage technique may be utilized to store data without a standard format. Data sets may be stored using any suitable technique, including, for example, storing individual files using an ISO/IEC 7816-4 file structure; implementing a domain whereby a dedicated file is selected that exposes one or more elementary files containing one or more data sets; using data sets stored in individual files using a hierarchical filing system; data sets stored as records in a single file (including compression, SQL accessible, hashed via one or more keys, numeric, alphabetical by first tuple, etc.); Binary Large Object (BLOB); stored as ungrouped data elements encoded using ISO/IEC 7816-6 data elements; stored as ungrouped data elements encoded using ISO/IEC Abstract Syntax Notation (ASN.1) as in ISO/IEC 8824 and 8825; and/or other proprietary techniques that may include fractal compression methods, image compression methods, etc.

In various embodiments, the ability to store a wide variety of information in different formats is facilitated by storing the information as a BLOB. Thus, any binary information can be stored in a storage space associated with a data set. As discussed above, the binary information may be stored on the financial transaction instrument or external to but affiliated with the financial transaction instrument. The BLOB method may store data sets as ungrouped data elements formatted as a block of binary via a fixed memory offset using either fixed storage allocation, circular queue techniques, or best practices with respect to memory management (e.g., paged memory, least recently used, etc.). By using BLOB methods, the ability to store various data sets that have different formats facilitates the storage of data associated with system 100 by multiple and unrelated owners of the data sets. For example, a first data set which may be stored may be provided by a first party, a second data set which may be stored may be provided by an unrelated second party, and yet a third data set which may be stored, may be provided by an third party unrelated to the first and second party. Each of these three exemplary data sets may contain different information that is stored using different data storage formats and/or techniques. Further, each data set may contain subsets of data that also may be distinct from other subsets.

As stated above, in various embodiments of system 100, the data can be stored without regard to a common format. However, in one exemplary embodiment, the data set (e.g., BLOB) may be annotated in a standard manner when provided for manipulating the data onto the financial transaction instrument. The annotation may comprise a short header, trailer, or other appropriate indicator related to each data set that is configured to convey information useful in managing the various data sets. For example, the annotation may be called a "condition header", "header", "trailer", or "status", herein, and may comprise an indication of the status of the data set or may include an identifier correlated to a specific issuer or owner of the data. In one example, the first three bytes of each data set BLOB may be configured or configurable to indicate the status of that particular data set; e.g., LOADED, INITIALIZED, READY, BLOCKED, REMOVABLE, or DELETED. Subsequent bytes of data may be used to indicate for example, the identity of the issuer, user, transaction/membership account identifier or the like. Each of these condition annotations are further discussed herein.

The data set annotation may also be used for other types of status information as well as various other purposes. For example, the data set annotation may include security information establishing access levels. The access levels may, for example, be configured to permit only certain individuals, levels of employees, companies, or other entities to access data sets, or to permit access to specific data sets based on the transaction, issuer, user or the like. Furthermore, the security information may restrict/permit only certain actions such as accessing, modifying, and/or deleting data sets. In one example, the data set annotation indicates that only the data set owner or the user are permitted to delete a data set, various identified users may be permitted to access the data set for reading, and others are altogether excluded from accessing the data set. However, other access restriction parameters may also be used allowing various entities to access a data set with various permission levels as appropriate.

The data, including the header or trailer may be received by a stand-alone interaction device configured to add, delete, modify, or augment the data in accordance with the header or trailer. As such, in various embodiments, the header or trailer is not stored on the transaction device along with the associated issuer-owned data but instead the appropriate action may be taken by providing to the transaction instrument user at the stand-alone device, the appropriate option for the action to be taken. System 100 contemplates a data storage arrangement wherein the header or trailer, or header or trailer history, of the data is stored on the transaction instrument in relation to the appropriate data.

One skilled in the art will also appreciate that, for security reasons, any databases, systems, devices, servers or other components of system 100 may consist of any combination thereof at a single location or at multiple locations, wherein each database or system 100 includes any of various suitable security features, such as firewalls, access codes, encryption, decryption, compression, decompression, and/or the like.

Various databases used herein may include: client data; provider data; financial institution data; and/or like data useful in the operation of the present disclosure. As those skilled in the art will appreciate, user computer may include an operating system (e.g., Windows NT, 95/98/2000/XP/VISTA/7, OS2, UNIX, Linux, Solaris, MacOS, etc.) as well as various conventional support software and drivers typically associated with computers. The computer may include any suitable personal computer, network computer, workstation, minicomputer, mainframe or the like. User computer can be in a home or business environment with access to a network. In various embodiments, access is through a network or the Internet through a commercially-available web-browser software package.

As used herein, the term "network" shall include any electronic communications means which incorporates both hardware and software components of such. Communication among the parties in accordance with the present disclosure may be accomplished through any suitable communication channels, such as, for example, a telephone network, an extranet, an intranet, Internet, point of interaction device (point of sale device, personal digital assistant, cellular phone, kiosk, etc.), online communications, satellite communications, off-line communications, wireless communications, transponder communications, local area network (LAN), wide area network (WAN), networked or linked devices, keyboard, mouse and/or any suitable communication or data input modality. Moreover, although the disclosure is frequently described herein as being implemented with TCP/IP communications protocols, the disclosure may also be implemented using IPX, Appletalk, IP-6, NetBIOS, OSI or any number of existing or future protocols. If the network is in the nature of a public network, such as the Internet, it may be advantageous to presume the network to be insecure and open to eavesdroppers. Specific information related to the protocols, standards, and application software utilized in connection with the Internet is generally known to those skilled in the art and, as such, need not be detailed herein. See, for example, Dilip Naik, Internet Standards And Protocols (1998); Java 2 Complete, various authors, (Sybex 1999); Deborah Ray And Eric Ray, Mastering Html 4.0 (1997); and Loshin, TCP/IP Clearly Explained (1997) and David Gourley and Brian Totty, HTTP, The Definitive Guide (2002), the contents of which are hereby incorporated by reference.

The disclosure may be described herein in terms of functional block components, screen shots, optional selections and various processing steps. It should be appreciated that such functional blocks may be realized by any number of hardware and/or software components configured to perform the specified functions. For example, system 100 may employ various integrated circuit components, e.g., memory elements, processing elements, logic elements, look-up tables, and/or the like, which may carry out a variety of functions under the control of one or more microprocessors or other control devices. Similarly, the software elements of system 100 may be implemented with any programming or scripting language such as C, C++, Java, COBOL, assembler, PERL, Visual Basic, SQL Stored Procedures, extensible markup language (XML), with the various algorithms being implemented with any combination of data structures, objects, processes, routines or other programming elements. Further, it should be noted that system 100 may employ any number of conventional techniques for data transmission, signaling, data processing, network control, and/or the like. Still further, system 100 could be used to detect or prevent security issues with a client-side scripting language, such as JavaScript, VBScript or the like. For a basic introduction of cryptography and network security, see any of the following references: (1) "Applied Cryptography: Protocols, Algorithms, And Source Code In C," by Bruce Schneier, published by John Wiley & Sons (second edition, 1995); (2) "Java Cryptography" by Jonathan Knudson, published by O'Reilly & Associates (1998); (3) "Cryptography & Network Security: Principles & Practice" by William Stallings, published by Prentice Hall; all of which are hereby incorporated by reference.

These software elements may be loaded onto a general purpose computer, special purpose computer, or other programmable data processing apparatus to produce a machine, such that the instructions that execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, may be implemented by either special purpose hardware-based computer systems which perform the specified functions or steps, or suitable combinations of special purpose hardware and computer instructions. Further, illustrations of the process flows and the descriptions thereof may make reference to user windows, web pages, web sites, web forms, prompts, etc. Practitioners will appreciate that the illustrated steps described herein may comprise in any number of configurations including the use of windows, web pages, web forms, popup windows, prompts and/or the like. It should be further appreciated that the multiple steps as illustrated and described may be combined into single web pages and/or windows but have been expanded for the sake of simplicity. In other cases, steps illustrated and described as single process steps may be separated into multiple web pages and/or windows but have been combined for simplicity.

Practitioners will appreciate that there are a number of methods for displaying data within a browser-based document. Data may be represented as standard text or within a fixed list, scrollable list, drop-down list, editable text field, fixed text field, pop-up window, and/or the like. Likewise, there are a number of methods available for modifying data in a web page such as, for example, free text entry using a keyboard, selection of menu items, check boxes, option boxes, and/or the like.

In various embodiments and with continued reference to FIG. 1, a UPAS 140 may further comprise user information engine 150, user profile module 155, risk module 160, advertising engine 165, and the like. These engines and modules may be separately or jointly configured to acquire user information, display user information, complete user initiated administrative tasks, and provide advertisements to user 105.

User information engine 150 may be any hardware and/or software configured to acquire first user information. First user information may be acquired before a visit, after a visit, and/or during a visit to a healthcare provider. This user information can be combined to create a user profile. For example, user 105 may provide health information via an electronic scheduling service in advance of an appointment, or to the doctor during the appointment. This information may include various demographic and health information (e.g. age, sex, weight, symptoms, etc.). This information may be captured by user information engine 150 before a user (e.g., patient) sees the doctor or during the doctor visit. The patient may also have medical history information (e.g. pre-existing medical conditions such as high blood pressure, prior procedures, chronic conditions, etc.). Such information may be captured by user information engine 150 through patient electronic medical/health records, medical billings (e.g., prior billings), medical billing codes, third party databases (e.g. third party electronic medical/health records provider), and/or through various other channels, such as on-line medical messaging services. This information may be captured by user information engine 150, before, during, or after the patient receives medical care.

Figure 2:
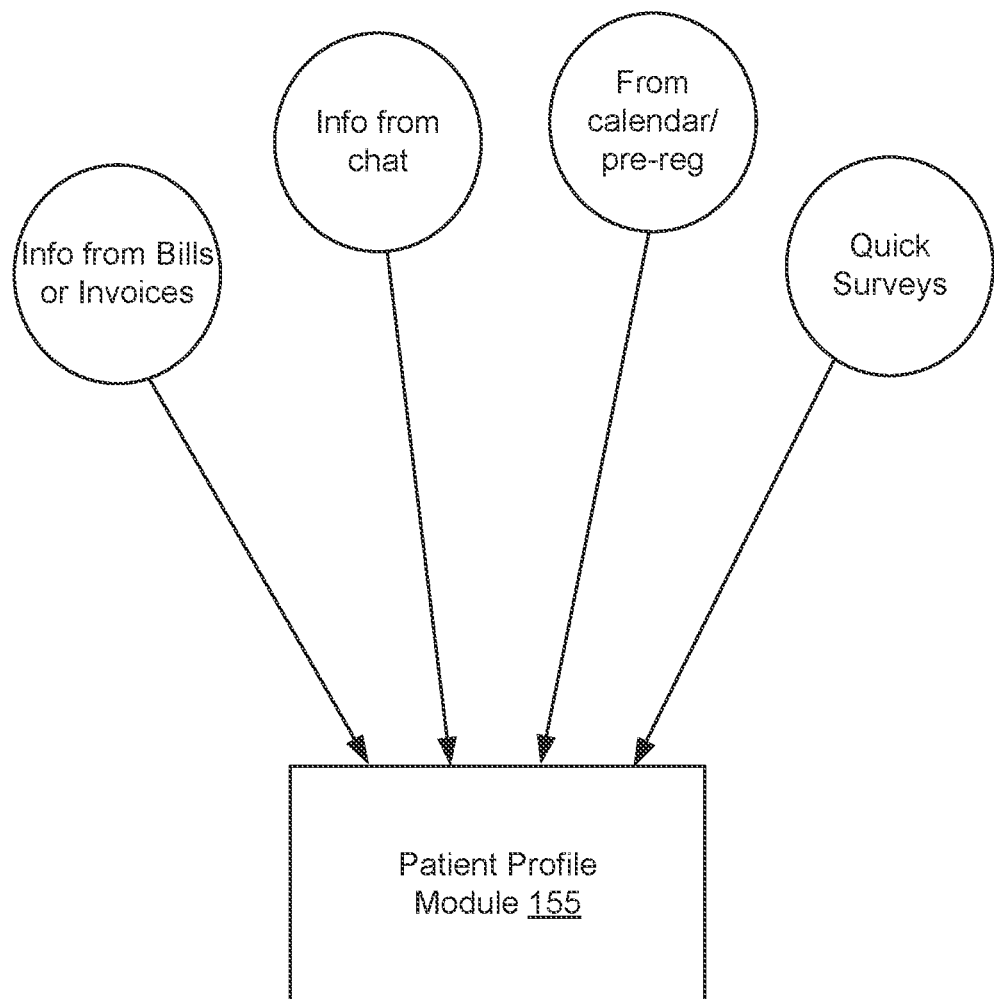
FIG. 2 is a block diagram illustrating an exemplary data source for a user profile module, in accordance with various embodiments.

User profile module 155 may be any hardware and/or software configured to receive, combine, compile, display, transmit or create a profile for a user. User information engine 150 may provide or combine first user information with other user information, such as an existing user profile, an electronic medical/health record, or other information, as shown in FIG. 2. For example, a user that uses a UPAS 140 may have a user profile, wherein user profile module 155 collects various medical information provided by user information engine 150 to supplement the information in the user profile.

Figure 3:
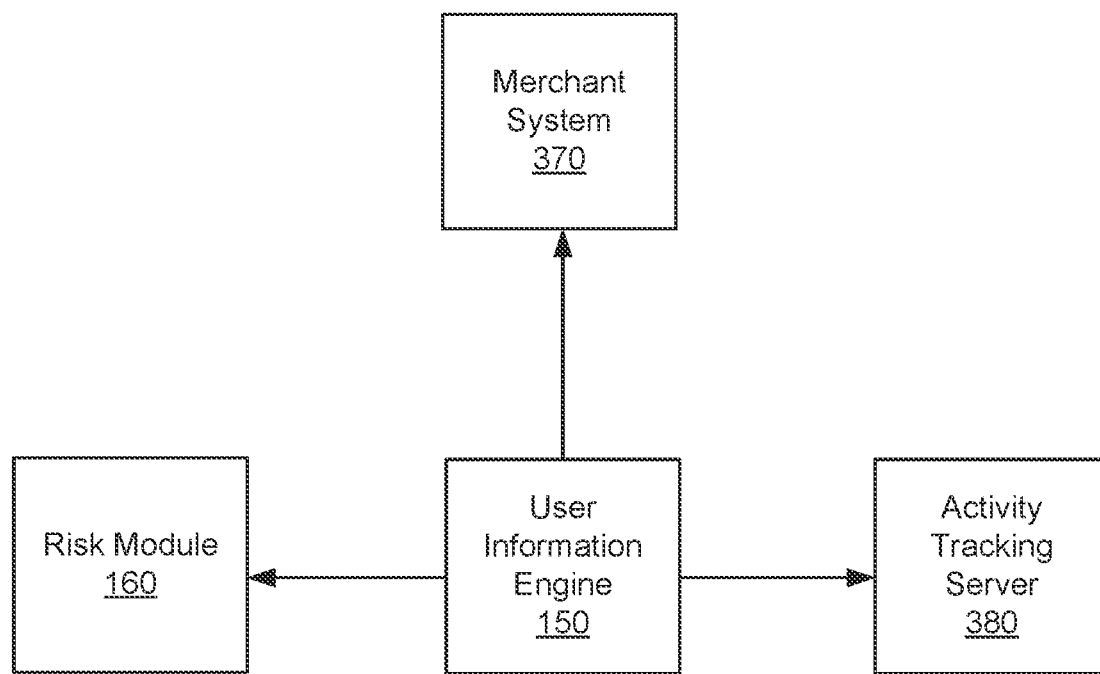
FIG. 3 is diagram illustrating a customer evaluation portion of an exemplary system for providing an advertisement to a user in accordance with various embodiments.

In various embodiments, and with reference to FIG. 1 and FIG. 3, risk module 160 may be any suitable module that is configured to determine the risk associated with a user. Risk module 160 may receive information from merchant system 370 and/or activity tracking service 380 via user information engine 150. In this regard, user information engine 150 is configured to connect to and/or receive data from merchant system 370 and/or activity tracking service 380. For example, user information engine 150 may receive transaction information as discussed herein from a merchant via merchant system 370. User information engine 150 may be configured to analyze the transaction information to determine what kinds of items were purchased by a user and what type of health impact those items may have on the user. This information may be equated to a health impact parameter that can be evaluated by risk module 160. Risk module 160 may be configured to determine an overall health risk for a user based on the various items purchased form a merchant and identified by the user information engine 150. Moreover, risk module 160 may be able to make this assessment continuously or nearly continuously based on the routine activities of the user to create a holistic risk assessment based on the items purchased through merchant system 370.

User information engine 150 may be further configured to connect to and/or receive data from activity tracking service 380. For example, user information engine 150 may collect data from activity tracking service 380 about activity and/or exercise by user 105. As discussed herein, activity tracking service 380 may be a local system that includes a wearable and a smartphone and/or computer interface such as, for example, a Fitbit available from Fitbit, Inc., and/or the like. Activity tracking service 380 may also include a network tracking service that includes a smartphone interface such as, for example, Strava, provided by Strava, Inc. and/or the like. User information engine 150 may be configured to analyze the activity information to determine what kind of activities were performed by a user and what type of health impact those activities may have on the user. This information may be equated to a health impact parameter that can be evaluated by risk module 160. Risk module 160 may be configured to determine an overall health risk for a user based on the various activities performed by the user and identified by the user information engine 150. Moreover, risk module 160 may be able to make this assessment continuously or nearly continuously based on the routine activities of the user to create a holistic risk assessment as a function of the activities of the user that are tracked by activity tracking service 380.

Figure 4:
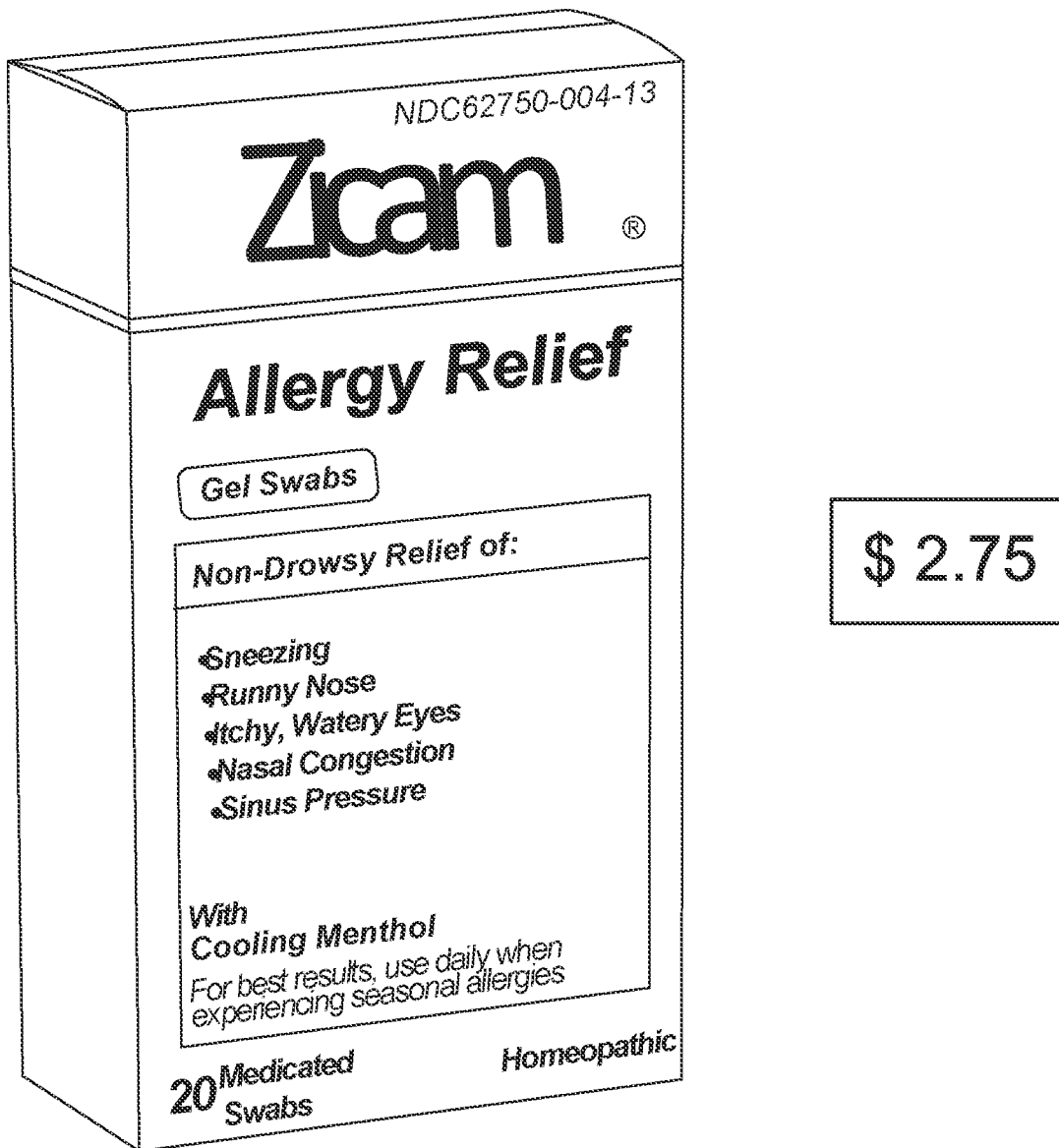
FIG. 4 is diagram illustrating an exemplary advertisement provided in accordance with various embodiments.

Advertising engine 165 may be any hardware and/or software configured to collect and analyze user information and/or access and analyze a user profile. Advertising engine 165 may be configured to parse user data and provide targeted marketing in connection with user data. For example, in response to a user action (e.g. upon logging into a user payment system, processing a bill in a user payment system, to connecting to an on-line messenger in a user payment system, in the middle of two steps during a pre-registration or scheduling an appointment in a user payment system, etc.), advertising engine 165 is configured to display an advertisement, as shown in FIG. 4, for an item which relates to the user information provided by user information engine 150 or user profile module 155 (e.g. an advertisement for a new diabetes medication would be displayed to a diabetic user with symptoms corresponding to those the medication is intended to treat). In various embodiments, advertising engine 165 may be configured to display multiple advertisements.

Advertising engine 165 may be an advertising program within various user payment systems 140 and similar systems, including for example, bill view, payment pages, financing, point of sale software, messenger software, healthcare scheduling systems (e.g. MedPayonline's e-visit tool), pre-registration, scheduling, etc. Advertisements provided by advertising engine 165 may be directed to health, pharmaceuticals, hospital services, over the counter medicines, and various different health related services and products. Revenue may be aggregated into an account from advertising revenue and may be allocated in number of ways (the allocations do not have to be equal), including for example: 1) a portion of revenue may be allocated to provide discounts to paying users; 2) a portion of revenue may be allocated to the hospital/health care provider; 3) a portion of the revenue may be allocated to the user payment system provider.

UPAS 140 may be configured to allocate advertising revenue from ads provided by advertising engine 165. The UPAS 140 may be configured to allocate money or "credits" earned in connection with add revenue to a user's payment, balance, or account. For example, each advertisement may have a pre-determined value, such that a percentage of that value is allocated to user 105 each time the advertisement is displayed. After the advertisement is displayed, user 105 may select to apply their funds to a current payment, an outstanding balance or save them in account.

With respect to the particular method of allocating funds, any known or developed system for applying debits and credits to accounts may be used. In various embodiments, advertising revenue may used immediately or deposited in an account, such as for example a payment service account (e.g. Paypal), a traditional bank account, or in an account provided by the user payment system provider. For example, if the user decides to utilize their funds immediately, the user's funding source (e.g. a user's credit card or user's bank account) will be charged the payment due amount minus the user's share of advertising revenue. At the time of payment or potentially at the end of each business day (depending on the funding source), user payment system provider may disperse the user's share of the advertising revenue to the medical provider in the name of the user and/or patient. If the user decides to use the funds at a later date, the user payment system account may be credited with the user's portion of the advertising revenue, which may be used at any time for a medical payment through the user payment system.

Similarly, the healthcare provider's portion of the advertising revenue may be dispersed (e.g., once a day) to the healthcare provider's account, such as for example, a payment services account (e.g. Paypal), a traditional bank account, and/or the like. The healthcare provider's portion of the advertising revenue may be distributed to the provider immediately (e.g. each business day), applied to a healthcare provider account provided by a user payment account provider, and/or applied to current or future processing fees. The user payment system provider's portion of the advertising revenue may be distributed to the user payment system provider's account in any way known in the art or subsequently developed.

Figure 5:
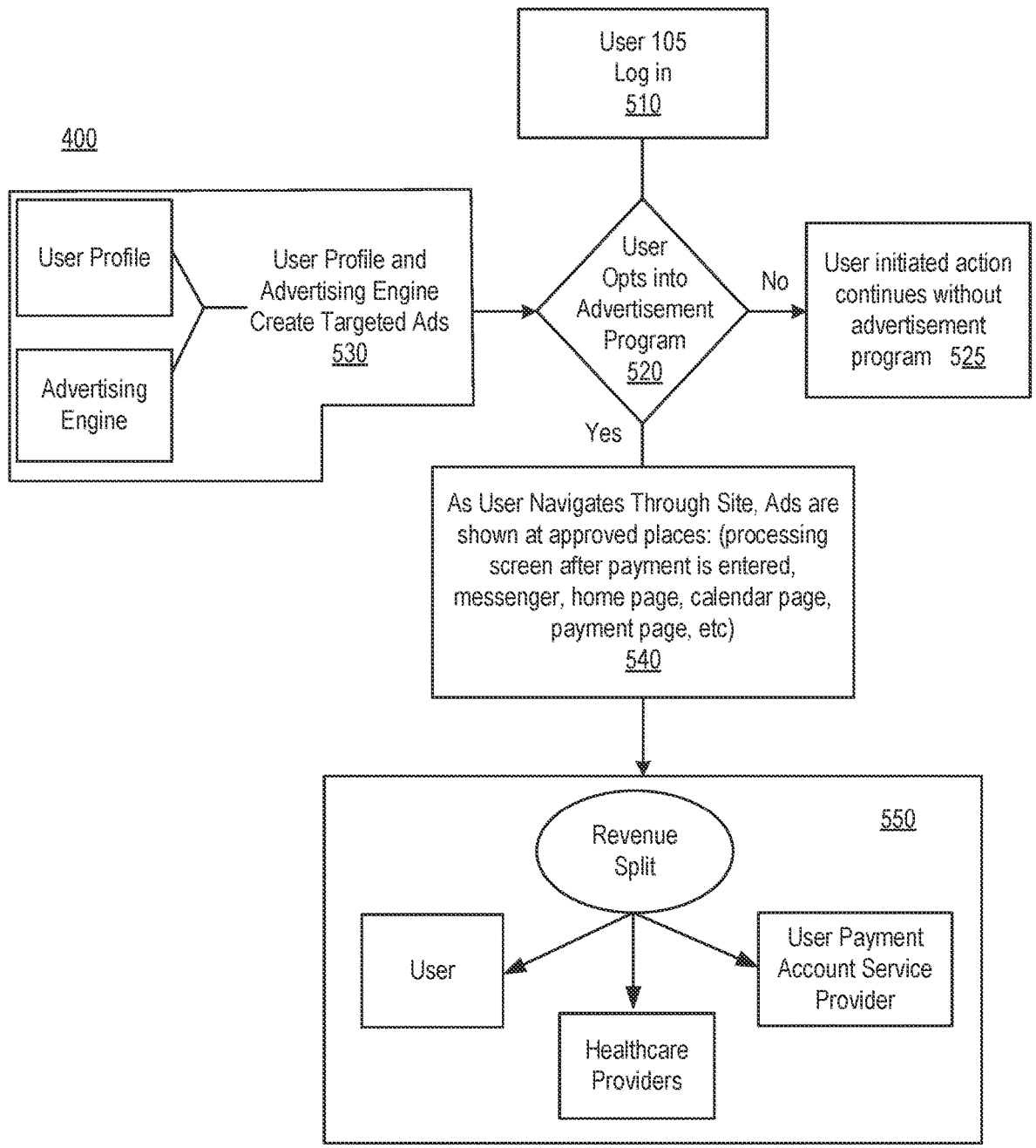
FIG. 5 is a flow chart illustrating an exemplary process displaying advertisements and allocated advertising revenue, in accordance with various embodiments.

In summary, with respect to an exemplary method, and with reference to FIG. 5, a user payment advertising revenue distribution system is provided. User may access UPAS 140 (Step 510). Upon logging into the system, user 105 may have the option to take part in an advertising program provided via advertising engine 165 (Step 520). If user 105 chooses not to participate in the advertising program, the user initiated action continues without any action from advertising engine 165 (Step 525). If the user chooses to participate in the advertising program, advertising engine 165 may select or create advertisements based on user information, for example information from user profile, providing for targeted marketing (Step 530). As user 105 navigates through UPAS 140, advertisements are provided at specific points (e.g. setting up an account, making a payment, conversing online via messenger, or initiating another action the system) (Step 540). In response to user 105 participating in the program, a certain percentage of the revenue generated by the advertisements may be applied to a user account (Step 550). User 105 may apply all or a portion of the revenue in the account to a payment, bill, balance or maintain a balance in the account to accrue interest such that the money or credits in the account may be used for a future payment by the user. Further, advertising revenue may be allocated to a healthcare provider and/or a user payment account service provider, as shown in Step 550.

In various embodiments, and with reference to FIG. 6, system 100 may be configured to execute a method 600 for patient modeling based on items purchase and activities of a user. Method 600 may comprise requesting first data from a merchant associated with a user and second data from an activity tracking service associated with user 105 (step 610). In this regard, user information engine 150 may be configured to interface with a merchant system via, for example, an API. The merchant system may be any suitable system that is operated by a merchant that provides information about items purchased by a particular user. The items purchased by the particular user may be anonymized in some fashion. For example, the amount paid for each item, the instrument used to pay for the item, and/or any other financial details about the item may be removed to protect certain levels of user confidentiality.

In various embodiments, user information engine 150 may also be in communication with an activity tracking service via, for example, an API, a Bluetooth connection, and/or any other suitable internet communication protocol or short range electronic communication protocol. The activity tracking service may be associated with user 105. For example, the activity tracking service may be a health monitoring device or wearable that is associated with and/or worn by user 105 to track steps of user 105, movement, vital signs (e.g., heart rate, blood pressure, and/or the like), exercise level, and/or the like. This activity tracking service or/and wearable may be, for example, a fit bit, and/or other suitable device that is capable of monitoring user vital sign and/or activity level. The activity tracking service may also be a service that tracks food and/or nutrition consumed by user 105 or fitness activities performed by user 105. The activity tracking service may have a micro-application associated with user's 105 phone or wearable that allows user 105 to input data or activate activity monitoring periods. For example, user 105 may use an application to monitor calories and/or nutrition consumed by user 105 such as, for example, My Fitness Pal. User 105 may also use an application to monitor exercise such as, for example, Map My Run, Strava, and/or like.

In various embodiments, method 600 may further comprise parsing the first data to determine an item purchased from user 105 (step 620). The first data received from the merchant may include more information than a particular item identifier. In this regard, the data may be parsed and/or filtered to identify a particular item purchased from the merchant by user 105. For example, an item identifier may be compared to a database or look up table of item identifiers to identify a particular item purchased by user 105. Method 600 may further comprise analyzing the item to determine a first health impact for the item based on the item and the demographic information associated with user 105 (step 630). Each item purchased by a user may be analyzed to determine a health impact for user 105 based on information about user 105. In this regard, certain items may have different health impacts for particular items may have particular health impacts for a particular user demographic and/or other health information of user 105.

In various embodiments, method 600 may further comprise parsing the second data to determine a level of activity monitored by the activity tracking service (step 640). The second data may be analyzed to determine the extent of activity associated with user 105. Method 600 may further comprise analyzing the level of activity to determine a second health impact from the level of activity based on the level of activity and the demographic information associated with user 105 (step 650). In this regard the level of activity may be associated with and/or may influence a factor or health impact that is associated with user 105.

In various embodiments, method 600 may further comprise evaluating a health risk of user 105 based on the first health impact, the second health impact, and the demographic information associated with user 105 (Step 670). The first data associated with the item purchased and the second data associated with the level of activity monitor by the activity tracking service may be indicative of and/or may be quantified herein as a first health impact or a second health impact respectively. These health impacts may be evaluated against the demographic information associated with user 105 to determine whether particular items are harmful and/or increase the risk associated with the health of user 105. Moreover, the health risk may be indicative of and/or associated with a particular health condition. Moreover the first health impact and/or the second health impact may similarly be associated with a medical condition this medical condition may be analyzed by system 100.

In various embodiments, method 600 may further comprise selecting an advertisement based on medical data and at least one of the first health impact, the second health impact, or the demographic information associated with user 105 (step 670). In this regard, the user information engine 150 may access user profile module 155 and/or risk module 160. Based on the information from profile module 155 and/or risk module 160, patient information engine and advertising engine may select an advertisement that is tailored for the user based on the attribute and/or health condition of user 105. In this regard, advertisements provided by advertising engine 165 and presented to user 105 through user payment system 140 are tailored to user 105 and the particular ailments or needs associated with the activities of user 105 and/or the items consumed by user 105. Moreover, this tailoring evaluation and/or analysis may be conducted by system 100 in advance of, during, and/or after a user's visit to a health care provider and/or medical facility. Moreover, method 600 may be continuously executed by system 100 to model the particular behaviors and/or attributes associated with a particular user 105. In this way, the advertisements selected for a user are tailored to the activities of user 105 and items consumed by user 105.

The disclosure and claims do not describe only a particular outcome of providing incentives, but the disclosure and claims include specific rules for implementing the outcome of providing incentives and that render information into a specific format that is then used and applied to create the desired results of providing incentives, as set forth in McRO, Inc. v. Bandai Namco Games America Inc. (Fed. Cir. case number 15-1080, Sep. 13, 2016). In other words, the outcome of providing incentives can be performed by many different types of rules and combinations of rules, and this disclosure includes various embodiments with specific rules. While the absence of complete preemption may not guarantee that a claim is eligible, the disclosure does not sufficiently preempt the field of providing incentives at all. The disclosure acts to narrow, confine, and otherwise tie down the disclosure so as not to cover the general abstract idea of just providing incentives. Significantly, other systems and methods exist for providing incentives, so it would be inappropriate to assert that the claimed invention preempts the field or monopolizes the basic tools of providing incentives. In other words, the disclosure will not prevent others from providing incentives, because other systems are already performing the functionality in different ways than the claimed invention. Moreover, the claimed invention includes an inventive concept that may be found in the non-conventional and non-generic arrangement of known, conventional pieces, in conformance with Bascom v. AT&T Mobility, 2015-1763 (Fed. Cir. 2016). The disclosure and claims go way beyond any conventionality of any one of the systems in that the interaction and synergy of the systems leads to additional functionality that is not provided by any one of the systems operating independently. The disclosure and claims may also include the interaction between multiple different systems, so the disclosure cannot be considered an implementation of a generic computer, or just "apply it" to an abstract process. The disclosure and claims may also be directed to improvements to software with a specific implementation of a solution to a problem in the software arts.

In various embodiments, the system and method may include alerting a subscriber when their computer is offline. The system may include generating customized information and alerting a remote subscriber that the information can be accessed from their computer. The alerts are generated by filtering received information, building information alerts and formatting the alerts into data blocks based upon subscriber preference information. The data blocks are transmitted to the subscriber's wireless device which, when connected to the computer, causes the computer to auto-launch an application to display the information alert and provide access to more detailed information about the information alert. More particularly, the method may comprise providing a viewer application to a subscriber for installation on the remote subscriber computer; receiving information at a transmission server sent from a data source over the Internet, the transmission server comprising a microprocessor and a memory that stores the remote subscriber's preferences for information format, destination address, specified information, and transmission schedule, wherein the microprocessor filters the received information by comparing the received information to the specified information; generates an information alert from the filtered information that contains a name, a price and a universal resource locator (URL), which specifies the location of the data source; formats the information alert into data blocks according to said information format; and transmits the formatted information alert over a wireless communication channel to a wireless device associated with a subscriber based upon the destination address and transmission schedule, wherein the alert activates the application to cause the information alert to display on the remote subscriber computer and to enable connection via the URL to the data source over the Internet when the wireless device is locally connected to the remote subscriber computer and the remote subscriber computer comes online.

In various embodiments, the system and method may include a graphical user interface for dynamically relocating/rescaling obscured textual information of an underlying window to become automatically viewable to the user. By permitting textual information to be dynamically relocated based on an overlap condition, the computer's ability to display information is improved. More particularly, the method for dynamically relocating textual information within an underlying window displayed in a graphical user interface may comprise displaying a first window containing textual information in a first format within a graphical user interface on a computer screen; displaying a second window within the graphical user interface; constantly monitoring the boundaries of the first window and the second window to detect an overlap condition where the second window overlaps the first window such that the textual information in the first window is obscured from a user's view; determining the textual information would not be completely viewable if relocated to an unobstructed portion of the first window; calculating a first measure of the area of the first window and a second measure of the area of the unobstructed portion of the first window; calculating a scaling factor which is proportional to the difference between the first measure and the second measure; scaling the textual information based upon the scaling factor; automatically relocating the scaled textual information, by a processor, to the unobscured portion of the first window in a second format during an overlap condition so that the entire scaled textual information is viewable on the computer screen by the user; and automatically returning the relocated scaled textual information, by the processor, to the first format within the first window when the overlap condition no longer exists.

In various embodiments, the system may also include isolating and removing malicious code from electronic messages (e.g., email) to prevent a computer from being compromised, for example by being infected with a computer virus. The system may scan electronic communications for malicious computer code and clean the electronic communication before it may initiate malicious acts. The system operates by physically isolating a received electronic communication in a "quarantine" sector of the computer memory. A quarantine sector is a memory sector created by the computer's operating system such that files stored in that sector are not permitted to act on files outside that sector. When a communication containing malicious code is stored in the quarantine sector, the data contained within the communication is compared to malicious code-indicative patterns stored within a signature database. The presence of a particular malicious code-indicative pattern indicates the nature of the malicious code. The signature database further includes code markers that represent the beginning and end points of the malicious code. The malicious code is then extracted from malicious code-containing communication. An extraction routine is run by a file parsing component of the processing unit. The file parsing routine performs the following operations: scan the communication for the identified beginning malicious code marker; flag each scanned byte between the beginning marker and the successive end malicious code marker; continue scanning until no further beginning malicious code marker is found; and create a new data file by sequentially copying all non-flagged data bytes into the new file, which thus forms a sanitized communication file. The new, sanitized communication is transferred to a non-quarantine sector of the computer memory. Subsequently, all data on the quarantine sector is erased. More particularly, the system includes a method for protecting a computer from an electronic communication containing malicious code by receiving an electronic communication containing malicious code in a computer with a memory having a boot sector, a quarantine sector and a non-quarantine sector; storing the communication in the quarantine sector of the memory of the computer, wherein the quarantine sector is isolated from the boot and the non-quarantine sector in the computer memory, where code in the quarantine sector is prevented from performing write actions on other memory sectors; extracting, via file parsing, the malicious code from the electronic communication to create a sanitized electronic communication, wherein the extracting comprises scanning the communication for an identified beginning malicious code marker, flagging each scanned byte between the beginning marker and a successive end malicious code marker, continuing scanning until no further beginning malicious code marker is found, and creating a new data file by sequentially copying all non-flagged data bytes into a new file that forms a sanitized communication file; transferring the sanitized electronic communication to the non-quarantine sector of the memory; and deleting all data remaining in the quarantine sector.

In various embodiments, the system may also address the problem of retaining control over customers during affiliate purchase transactions, using a system for co-marketing the "look and feel" of the host web page with the product-related content information of the advertising merchant's web page.

The system can be operated by a third-party outsource provider, who acts as a broker between multiple hosts and merchants. Prior to implementation, a host places links to a merchant's webpage on the host's web page. The links are associated with product-related content on the merchant's web page. Additionally, the outsource provider system stores the "look and feel" information from each host's web pages in a computer data store, which is coupled to a computer server. The "look and feel" information includes visually perceptible elements such as logos, colors, page layout, navigation system, frames, mouse-over effects or other elements that are consistent through some or all of each host's respective web pages. A customer who clicks on an advertising link is not transported from the host web page to the merchant's web page, but instead is re-directed to a composite web page that combines product information associated with the selected item and visually perceptible elements of the host web page. The outsource provider's server responds by first identifying the host web page where the link has been selected and retrieving the corresponding stored "look and feel" information. The server constructs a composite web page using the retrieved "look and feel" information of the host web page, with the product-related content embedded within it, so that the composite web page is visually perceived by the customer as associated with the host web page. The server then transmits and presents this composite web page to the customer so that she effectively remains on the host web page to purchase the item without being redirected to the third party merchant affiliate. Because such composite pages are visually perceived by the customer as associated with the host web page, they give the customer the impression that she is viewing pages served by the host. Further, the customer is able to purchase the item without being redirected to the third party merchant affiliate, thus allowing the host to retain control over the customer. This system enables the host to receive the same advertising revenue streams as before but without the loss of visitor traffic and potential customers. More particularly, the system may be useful in an outsource provider serving web pages offering commercial opportunities. The computer store containing data, for each of a plurality of first web pages, defining a plurality of visually perceptible elements, which visually perceptible elements correspond to the plurality of first web pages; wherein each of the first web pages belongs to one of a plurality of web page owners; wherein each of the first web pages displays at least one active link associated with a commerce object associated with a buying opportunity of a selected one of a plurality of merchants; and wherein the selected merchant, the outsource provider, and the owner of the first web page displaying the associated link are each third parties with respect to one other; a computer server at the outsource provider, which computer server is coupled to the computer store and programmed to: receive from the web browser of a computer user a signal indicating activation of one of the links displayed by one of the first web pages; automatically identify as the source page the one of the first web pages on which the link has been activated; in response to identification of the source page, automatically retrieve the stored data corresponding to the source page; and using the data retrieved, automatically generate and transmit to the web browser a second web page that displays: information associated with the commerce object associated with the link that has been activated, and the plurality of visually perceptible elements visually corresponding to the source page.

Systems, methods and computer program products are provided. In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

As used herein, "satisfy", "meet", "match", "associated with" or similar phrases may include an identical match, a partial match, meeting certain criteria, matching a subset of data, a correlation, satisfying certain criteria, a correspondence, an association, an algorithmic relationship and/or the like. Similarly, as used herein, "authenticate" or similar terms may include an exact authentication, a partial authentication, authenticating a subset of data, a correspondence, satisfying certain criteria, an association, an algorithmic relationship and/or the like.

Terms and phrases similar to "associate" and/or "associating" may include tagging, flagging, correlating, using a look-up table or any other method or system for indicating or creating a relationship between elements, such as, for example, (i) a transaction account and (ii) an item (e.g., offer, reward, discount) and/or digital channel. Moreover, the associating may occur at any point, in response to any suitable action, event, or period of time. The associating may occur at pre-determined intervals, periodic, randomly, once, more than once, or in response to a suitable request or action. Any of the information may be distributed and/or accessed via a software enabled link, wherein the link may be sent via an email, text, post, social network input and/or any other method known in the art.

Any communication, transmission and/or channel discussed herein may include any system or method for delivering content (e.g. data, information, metadata, etc), and/or the content itself. The content may be presented in any form or medium, and in various embodiments, the content may be delivered electronically and/or capable of being presented electronically. For example, a channel may comprise a website or device (e.g., Facebook, YOUTUBE®, APPLE® TV®, PANDORA®, XBOX®, SONY® PLAYSTATION®), a uniform resource locator ("URL"), a document (e.g., a MICROSOFT® Word® document, a MICROSOFT® Excel® document, an ADOBE® .pdf document, etc.), an "ebook," an "emagazine," an application or microapplication (as described herein), an SMS or other type of text message, an email, facebook, twitter, MMS and/or other type of communication technology. In various embodiments, a channel may be hosted or provided by a data partner. In various embodiments, the distribution channel may comprise at least one of a merchant website, a social media website, affiliate or partner websites, an external vendor, a mobile device communication, social media network and/or location based service. Distribution channels may include at least one of a merchant website, a social media site, affiliate or partner websites, an external vendor, and a mobile device communication. Examples of social media sites include FACEBOOK©, FOURSQUARE©, TWITTER©, MYSPACE©, LINKEDIN©, and the like. Examples of affiliate or partner websites include AMERI- CAN EXPRESS©, GROUPON©, LIVINGSOCIAL©, and the like. Moreover, examples of mobile device communications include texting, email, and mobile applications for smartphones.

A "patient profile", "user profile" or "user profile data" may comprise any information or data about a user that describes an attribute associated with the user (e.g., a preference, an interest, demographic information, personally identifying information, and the like).

In various embodiments, the methods described herein are implemented using the various particular machines described herein. The methods described herein may be implemented using the below particular machines, and those hereinafter developed, in any suitable combination, as would be appreciated immediately by one skilled in the art. Further, as is unambiguous from this disclosure, the methods described herein may result in various transformations of certain articles.

For the sake of brevity, conventional data networking, application development and other functional aspects of the systems (and components of the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical system.

The various system components discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various databases used herein may include: client data; merchant data; financial institution data; and/or like data useful in the operation of the system. As those skilled in the art will appreciate, user computer may include an operating system (e.g., WINDOWS®, OS2, UNIX®, LINUX®, SOLARIS®, MacOS, etc.) as well as various conventional support software and drivers typically associated with computers.

The present system or any part(s) or function(s) thereof may be implemented using hardware, software or a combination thereof and may be implemented in one or more computer systems or other processing systems. However, the manipulations performed by embodiments were often referred to in terms, such as matching or selecting, which are commonly associated with mental operations performed by a human operator. No such capability of a human operator is necessary, or desirable in most cases, in any of the operations described herein. Rather, the operations may be machine operations. Useful machines for performing the various embodiments include general purpose digital computers or similar devices.

In fact, in various embodiments, the embodiments are directed toward one or more computer systems capable of carrying out the functionality described herein. The computer system includes one or more processors, such as processor. The processor is connected to a communication infrastructure (e.g., a communications bus, cross-over bar, or network). Various software embodiments are described in terms of this exemplary computer system. After reading this description, it will become apparent to a person skilled in the relevant art(s) how to implement various embodiments using other computer systems and/or architectures. Computer system can include a display interface that forwards graphics, text, and other data from the communication infrastructure (or from a frame buffer not shown) for display on a display unit.

Computer system also includes a main memory, such as for example random access memory (RAM), and may also include a secondary memory. The secondary memory may include, for example, a hard disk drive and/or a removable storage drive, representing a floppy disk drive, a magnetic tape drive, an optical disk drive, etc. The removable storage drive reads from and/or writes to a removable storage unit in a well-known manner. Removable storage unit represents a floppy disk, magnetic tape, optical disk, etc. which is read by and written to by removable storage drive. As will be appreciated, the removable storage unit includes a computer usable storage medium having stored therein computer software and/or data.

In various embodiments, secondary memory may include other similar devices for allowing computer programs or other instructions to be loaded into computer system. Such devices may include, for example, a removable storage unit and an interface. Examples of such may include a program cartridge and cartridge interface (such as that found in video game devices), a removable memory chip (such as an erasable programmable read only memory (EPROM), or programmable read only memory (PROM)) and associated socket, and other removable storage units and interfaces, which allow software and data to be transferred from the removable storage unit to computer system.

Computer system may also include a communications interface. Communications interface allows software and data to be transferred between computer system and external devices. Examples of communications interface may include a modem, a network interface (such as an Ethernet card), a communications port, a Personal Computer Memory Card International Association (PCMCIA) slot and card, etc. Software and data transferred via communications interface are in the form of signals which may be electronic, electromagnetic, optical or other signals capable of being received by communications interface. These signals are provided to communications interface via a communications path (e.g., channel). This channel carries signals and may be implemented using wire, cable, fiber optics, a telephone line, a cellular link, a radio frequency (RF) link, wireless and other communications channels.

The terms "computer program medium" and "computer usable medium" and "computer readable medium" are used to generally refer to media such as removable storage drive and a hard disk installed in hard disk drive. These computer program products provide software to computer system.

Computer programs (also referred to as computer control logic) are stored in main memory and/or secondary memory. Computer programs may also be received via communications interface. Such computer programs, when executed, enable the computer system to perform the features as discussed herein. In particular, the computer programs, when executed, enable the processor to perform the features of various embodiments. Accordingly, such computer programs represent controllers of the computer system.

In various embodiments, software may be stored in a computer program product and loaded into computer system using removable storage drive, hard disk drive or communications interface. The control logic (software), when executed by the processor, causes the processor to perform the functions of various embodiments as described herein. In various embodiments, hardware components such as application specific integrated circuits (ASICs). Implementation of the hardware state machine so as to perform the functions described herein will be apparent to persons skilled in the relevant art(s).

In various embodiments, the server may include application servers (e.g. WEB SPHERE, WEB LOGIC, JBOSS, EDB® Postgres Plus Advanced Server® (PPAS), etc.). In various embodiments, the server may include web servers (e.g. APACHE, IIS, GWS, SUN JAVA® SYSTEM WEB SERVER).

A web client includes any device (e.g., personal computer) which communicates via any network, for example such as those discussed herein. Such browser applications comprise Internet browsing software installed within a computing unit or a system to conduct online transactions and/or communications. These computing units or systems may take the form of a computer or set of computers, although other types of computing units or systems may be used, including laptops, notebooks, tablets, hand held computers, personal digital assistants, set-top boxes, workstations, computer-servers, main frame computers, mini-computers, PC servers, pervasive computers, network sets of computers, personal computers, such as IPADS®, IMACS®, and MACBOOKS®, kiosks, terminals, point of sale (POS) devices and/or terminals, televisions, or any other device capable of receiving data over a network. A web-client may run MICROSOFT® INTERNET EXPLORER®, MOZILLA® FIREFOX®, GOOGLE® CHROME®, APPLE® Safari, or any other of the myriad software packages available for browsing the internet.

Practitioners will appreciate that a web client may or may not be in direct contact with an application server. For example, a web client may access the services of an application server through another server and/or hardware component, which may have a direct or indirect connection to an Internet server. For example, a web client may communicate with an application server via a load balancer. In various embodiments, access is through a network or the Internet through a commercially-available web-browser software package.

In various embodiments, components, modules, and/or engines of system 100 may be implemented as micro-applications or micro-apps. Micro-apps are typically deployed in the context of a mobile operating system, including for example, a WINDOWS® mobile operating system, an ANDROID® Operating System, APPLE® IOS®, a BLACKBERRY® operating system and the like. The micro-app may be configured to leverage the resources of the larger operating system and associated hardware via a set of predetermined rules which govern the operations of various operating systems and hardware resources. For example, where a micro-app desires to communicate with a device or network other than the mobile device or mobile operating system, the micro-app may leverage the communication protocol of the operating system and associated device hardware under the predetermined rules of the mobile operating system. Moreover, where the micro-app desires an input from a user, the micro-app may be configured to request a response from the operating system which monitors various hardware components and then communicates a detected input from the hardware to the micro-app.

As used herein, the term "network" includes any cloud, cloud computing system or electronic communications system or method which incorporates hardware and/or software components. Communication among the parties may be accomplished through any suitable communication channels, such as, for example, a telephone network, an extranet, an intranet, Internet, point of interaction device (point of sale device, personal digital assistant (e.g., IPHONE®, BLACKBERRY®), cellular phone, kiosk, etc.), online communications, satellite communications, off-line communications, wireless communications, transponder communications, local area network (LAN), wide area network (WAN), virtual private network (VPN), networked or linked devices, keyboard, mouse and/or any suitable communication or data input modality. Moreover, although the system is frequently described herein as being implemented with TCP/IP communications protocols, the system may also be implemented using IPX, APPLE® talk, IP-6, NetBIOS®, OSI, any tunneling protocol (e.g. IPsec, SSH), or any number of existing or future protocols. If the network is in the nature of a public network, such as the Internet, it may be advantageous to presume the network to be insecure and open to eavesdroppers. Specific information related to the protocols, standards, and application software utilized in connection with the Internet is generally known to those skilled in the art and, as such, need not be detailed herein. See, for example, DILIP NAIK, INTERNET STANDARDS AND PROTOCOLS (1998); JAVA® 2 COMPLETE, various authors, (Sybex 1999); DEBORAH RAY AND ERIC RAY, MASTERING HTML 4.0 (1997); and LOSHIN, TCP/IP CLEARLY EXPLAINED (1997) and DAVID GOURLEY AND BRIAN TOTTY, HTTP, THE DEFINITIVE GUIDE (2002), the contents of which are hereby incorporated by reference.

The various system components may be independently, separately or collectively suitably coupled to the network via data links which includes, for example, a connection to an Internet Service Provider (ISP) over the local loop as is typically used in connection with standard modem communication, cable modem, Dish Networks®, ISDN, Digital Subscriber Line (DSL), or various wireless communication methods, see, e.g., GILBERT HELD, UNDERSTANDING DATA COMMUNICATIONS (1996), which is hereby incorporated by reference. It is noted that the network may be implemented as other types of networks, such as an interactive television (ITV) network. Moreover, the system contemplates the use, sale or distribution of any goods, services or information over any network having similar functionality described herein.

"Cloud" or "Cloud computing" includes a model for enabling convenient, on-demand network access to a shared pool of configurable computing resources (e.g., networks, servers, storage, applications, and services) that can be rapidly provisioned and released with minimal management effort or service provider interaction. Cloud computing may include location-independent computing, whereby shared servers provide resources, software, and data to computers and other devices on demand. For more information regarding cloud computing, see the NIST's (National Institute of Standards and Technology) definition of cloud computing at http://csrc.nist.gov/publications/nistpubs/800-145/SP800-145.pdf (last visited June 2012), which is hereby incorporated by reference in its entirety.

As used herein, "transmit" may include sending electronic data from one system component to another over a network connection. Additionally, as used herein, "data" may include encompassing information such as commands, queries, files, data for storage, and the like in digital or any other form.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. Reference to an element in the singular is not intended to mean "one and only one" unless explicitly so stated, but rather "one or more." Moreover, where a phrase similar to 'at least one of A, B, or C' is used, it is intended that the phrase be interpreted to mean that A alone may be present in various embodiments, B alone may be present in various embodiments, C alone may be present in various embodiments, or that any combination of the elements A, B and C may be present in a single embodiment; for example, A and B, A and C, B and C, or A and B and C. All structural, chemical, and functional equivalents to the elements of the above-described exemplary embodiments that are known to those of ordinary skill in the art are expressly incorporated herein by reference and are intended to be encompassed by the disclosure. Further, a list of elements does not include only those elements but may include other elements not expressly listed or inherent to such process, method, article, or apparatus.

What is claimed is:

1. A method, comprising:
   parsing, by a processor, into a common format first data associated with an item purchased from a merchant and demographic information associated with a user;
   parsing, by the processor, into the common format second data associated with a level of activity monitored, tracked and collected by an activity tracking service,
   wherein the common format includes a merger of the first data and the second data, and
   wherein the first data and the second data are not in the common format;
   determining, by the processor, a first health impact of the item purchased from the merchant, based on the first data that is associated with the item and the demographic information associated with the user;
   continuously updating, by the processor, the first health impact based on subsequent items purchased from the merchant;
   determining, by the processor, a second health impact based on the level of activity, and the demographic information associated with the user;
   selecting, by the processor using an advertising engine, an advertisement based on medical data, and at least one of the first health impact, the second health impact or the demographic information associated with the user;
   presenting, by the processor, the advertisement to the user through a payment system of the user; and
   adjusting, by the processor, the advertisement based on the continuously updating of the first health impact.

2. The method of claim 1, further comprising:
   receiving, by the processor, a selection of a bill associated with the user; and
   allocating, by the processor, an incentive based on the advertisement.

3. The method of claim 1, wherein the selecting is further based on at least one of a profile of the user or a health risk associated with the user.

4. The method of claim 1, further comprising crediting, by the processor, an incentive from the advertisement to an account.

5. The method of claim 1, further comprising crediting, by the processor, an incentive from the advertisement to a bill associated with the user.

6. The method of claim 1, wherein the advertisement includes at least one of a product or a service associated with medical data associated with the user.

7. The method of claim 1, further comprising:
   receiving, by the processor, a selection of the advertisement;
   presenting, by the processor, an offer based on the advertisement for an offered item, wherein the offered item is associated with the medical data.

8. The method of claim 1, further comprising allocating, by the processor, at least a portion of revenue from the advertisement to at least one of the user, a health care provider or a user payment system provider.

9. The method of claim 1, further comprising displaying, by the processor, the advertisement in response to at least one of setting up an account in a user payment system, logging into the user payment system, processing a bill in the user payment system, connecting to an on-line messenger in the user payment system, being between two steps during a pre-registration or scheduling an appointment in the user payment system.

10. The method of claim 1, wherein the selecting the advertisement is performed by an advertising program within a user payment system.

11. The method of claim 1, wherein the second data relates to the activity tracking service.

12. The method of claim 1, further comprising merging, by the processor, the first data and the second data into the common format.

13. The method of claim 1, of further comprising determining, by the processor, kind of activities of the user from the second data that is associated with the level of activity monitored by the activity tracking service.

14. The method of claim 13, wherein the kind of activities include at least one of fitness activities or exercise activities.

15. The method of claim 1, further comprising removing, by the processor, an amount paid, transaction instrument used for payment or financial details from the first data.

16. The method of claim 1, further comprising requesting, by the processor, the first data from a merchant server of the merchant associated with the user and the second data from the activity tracking service associated with the user.

17. The method of claim 1, wherein the activity tracking service tracks at least one of steps, movement, vital signs or exercise level of the user.

18. A non-transitory tangible computer-readable storage medium having computer-executable instructions stored thereon that, if executed by a processor configured, causes the processor to perform a method comprising:
   parsing, by the processor, into a common format first data associated with an item purchased from a merchant and demographic information associated with a user;
   parsing, by the processor, into the common format second data associated with a level of activity monitored, tracked and collected by an activity tracking service,
   wherein the common format includes a merger of the first data and the second data, and
   wherein the first data and the second data are not in the common format;
   determining, by the processor, a first health impact of the item purchased from the merchant, based on the first data that is associated with the item and the demographic information associated with the user;
   continuously updating, by the processor, the first health impact based on subsequent items purchased from the merchant;
   determining, by the processor, a second health impact based on the level of activity, and the demographic information associated with the user;

selecting, by the processor using an advertising engine, an advertisement based on medical data, and at least one of the first health impact, the second health impact or the demographic information associated with the user;
presenting, by the processor, the advertisement to the user through a payment system of the user; and
adjusting, by the processor, the advertisement based on the continuously updating of the first health impact.

19. A system comprising:
a network interface communicating with a memory;
the memory communicating with a processor; and
the processor, when executing a computer program, is configured to perform operations comprising:
parsing, by the processor, into a common format first data associated with an item purchased from a merchant and demographic information associated with a user;
parsing, by the processor, into the common format second data associated with a level of activity monitored, tracked and collected by an activity tracking service,
wherein the common format includes a merger of the first data and the second data, and
wherein the first data and the second data are not in the common format;
determining, by the processor, a first health impact of the item purchased from the merchant, based on the first data that is associated with the item and the demographic information associated with the user;
continuously updating, by the processor, the first health impact based on subsequent items purchased from the merchant;
determining, by the processor, a second health impact based on the level of activity and the demographic information associated with the user;
selecting, by the processor using an advertising engine, an advertisement based on medical data, and at least one of the first health impact, the second health impact or the demographic information associated with the user;
presenting, by the processor, the advertisement to the user through a payment system of the user; and
adjusting, by the processor, the advertisement based on the continuously updating of the first health impact.

* * * * *